(12) United States Patent
Gillespie, Jr. et al.

(10) Patent No.: US 6,997,905 B2
(45) Date of Patent: Feb. 14, 2006

(54) DUAL ORIENTATION DISPLAY FOR A MEDICAL DEVICE

(75) Inventors: John Gillespie, Jr., Libertyville, IL (US); Thomas A. McGraghan, Libertyville, IL (US)

(73) Assignee: Baxter International Inc., Deerfield, IL (US)

( * ) Notice: Subject to any disclaimer, the term of this patent is extended or adjusted under 35 U.S.C. 154(b) by 568 days.

(21) Appl. No.: 10/172,804

(22) Filed: Jun. 14, 2002

(65) Prior Publication Data
US 2003/0233071 A1    Dec. 18, 2003

(51) Int. Cl.
A61M 1/00        (2006.01)

(52) U.S. Cl. ....................................... 604/151

(58) Field of Classification Search ................ 604/151; 128/DIG. 12, DIG. 13, DIG. 6, DIG. 1, 920, 128/923; 705/2, 3
See application file for complete search history.

(56) References Cited

U.S. PATENT DOCUMENTS

| | | |
|---|---|---|
| 3,756,752 A | 9/1973 | Stenner |
| 3,771,694 A | 11/1973 | Kaminski |
| 3,809,871 A | 5/1974 | Howard et al. |
| 3,998,103 A | 12/1976 | Björklund et al. |
| 4,151,407 A | 4/1979 | McBride et al. |
| 4,199,307 A | 4/1980 | Jassawalla |
| 4,273,121 A | 6/1981 | Jassawalla |
| 4,277,226 A | 7/1981 | Archibald |
| 4,308,866 A | 1/1982 | Jelliffe et al. |
| 4,320,757 A | 3/1982 | Whitney et al. |
| 4,369,780 A | 1/1983 | Sakai |
| 4,398,908 A | 8/1983 | Siposs |
| 4,428,381 A | 1/1984 | Hepp |
| 4,443,216 A | 4/1984 | Chappell |
| 4,451,255 A | 5/1984 | Bujan et al. |
| 4,460,358 A | 7/1984 | Somerville et al. |
| 4,472,116 A | 9/1984 | Wenstrup |
| 4,487,604 A | 12/1984 | Iwatschenko et al. |
| 4,493,710 A | 1/1985 | King et al. |
| 4,496,351 A | 1/1985 | Hillel et al. |
| 4,511,352 A | 4/1985 | Theeuwes et al. |
| 4,529,401 A | 7/1985 | Leslie et al. |
| 4,544,369 A | 10/1985 | Skakoon et al. |
| 4,551,133 A | 11/1985 | Zegers de Beyl et al. |
| 4,559,038 A | 12/1985 | Berg et al. |
| 4,561,830 A | 12/1985 | Bradley |
| 4,565,542 A | 1/1986 | Berg |
| 4,596,550 A | 6/1986 | Troutner |

(Continued)

FOREIGN PATENT DOCUMENTS

CH         665955        6/1988

(Continued)

OTHER PUBLICATIONS

International Search Report for International Application No. PCT/US02/36963 of Applicant Baxter International Inc.

(Continued)

*Primary Examiner*—Sharon Kennedy
(74) *Attorney, Agent, or Firm*—Austin J. Foley; Bell, Boyd & Lloyd LLC (57) ABSTRACT

A medical device (10) is disclosed. The device (10) is adaptable for configuration in various positions. In the preferred embodiment, the device (10) comprises an infusion pump (12) for dispensing a medical fluid to a patient. A controller (14) is operably connected to a display (16) and the pump (12). The display (16) is operably responsive to the position of the pump (10) wherein information on the display (16) can be easily viewed.

39 Claims, 3 Drawing Sheets

U.S. PATENT DOCUMENTS

| | | | |
|---|---|---|---|
| 4,601,702 | A | 7/1986 | Hudson |
| 4,602,249 | A | 7/1986 | Abbott |
| 4,624,661 | A | 11/1986 | Arimond |
| 4,637,817 | A | 1/1987 | Archibald et al. |
| 4,648,812 | A | 3/1987 | Kobayashi et al. |
| 4,650,469 | A | 3/1987 | Berg et al. |
| 4,652,262 | A | 3/1987 | Veracchi |
| 4,676,776 | A | 6/1987 | Howson |
| 4,681,563 | A | 7/1987 | Deckert et al. |
| 4,690,673 | A | 9/1987 | Bloomquist |
| 4,696,671 | A | 9/1987 | Epstein et al. |
| 4,718,576 | A | 1/1988 | Tamura et al. |
| 4,722,224 | A | 2/1988 | Scheller et al. |
| 4,722,734 | A | 2/1988 | Kolln |
| 4,725,205 | A | 2/1988 | Cannon et al. |
| 4,731,058 | A | 3/1988 | Doan |
| 4,741,732 | A | 5/1988 | Crankshaw et al. |
| 4,754,401 | A | 6/1988 | Kaczynski et al. |
| 4,756,706 | A | 7/1988 | Kerns et al. |
| 4,810,243 | A | 3/1989 | Howson |
| 4,836,752 | A | 6/1989 | Burkett |
| 4,838,857 | A | 6/1989 | Strowe et al. |
| 4,854,324 | A | 8/1989 | Hirschman et al. |
| 4,886,431 | A | 12/1989 | Soderquist et al. |
| 4,908,017 | A | 3/1990 | Howson et al. |
| 4,923,375 | A | 5/1990 | Ejlersen |
| 4,931,041 | A | 6/1990 | Faeser |
| 4,936,760 | A | 6/1990 | Williams |
| 4,941,808 | A | 7/1990 | Qureshi et al. |
| 4,943,279 | A | 7/1990 | Samiotes et al. |
| 4,954,046 | A | 9/1990 | Irvin et al. |
| 4,960,230 | A | 10/1990 | Marelli |
| 5,034,004 | A | 7/1991 | Crankshaw |
| 5,041,086 | A | 8/1991 | Koenig et al. |
| 5,053,031 | A | 10/1991 | Borsanyi |
| 5,055,001 | A | 10/1991 | Natwick et al. |
| 5,057,081 | A | 10/1991 | Sunderland |
| 5,061,243 | A | 10/1991 | Winchell et al. |
| 5,078,362 | A | 1/1992 | Lawless et al. |
| 5,078,683 | A | 1/1992 | Sancoff et al. |
| 5,088,904 | A | 2/1992 | Okada |
| 5,098,256 | A | 3/1992 | Smith |
| 5,098,377 | A | 3/1992 | Borsanyi et al. |
| 5,100,380 | A | 3/1992 | Epstein et al. |
| 5,104,374 | A | 4/1992 | Bishko et al. |
| 5,116,203 | A | 5/1992 | Natwick et al. |
| 5,120,096 | A | 6/1992 | D'Silva |
| 5,123,275 | A | 6/1992 | Daoud et al. |
| 5,131,816 | A | 7/1992 | Brown et al. |
| 5,135,500 | A | 8/1992 | Zdeb |
| 5,153,827 | A | 10/1992 | Coutré et al. |
| 5,160,320 | A | 11/1992 | Yum et al. |
| 5,165,874 | A | 11/1992 | Sancoff et al. |
| 5,176,004 | A | 1/1993 | Gaudet |
| 5,181,842 | A | 1/1993 | Sunderland et al. |
| 5,181,910 | A | 1/1993 | Scanlon |
| 5,213,483 | A | 5/1993 | Flaherty et al. |
| 5,219,327 | A | 6/1993 | Okada |
| 5,219,330 | A | 6/1993 | Bollish et al. |
| 5,219,331 | A | 6/1993 | Vanderveen |
| 5,219,428 | A | 6/1993 | Stern |
| 5,232,449 | A | 8/1993 | Stern et al. |
| 5,236,416 | A | 8/1993 | McDaniel et al. |
| 5,238,001 | A | 8/1993 | Gallant et al. |
| 5,242,408 | A | 9/1993 | Jhuboo et al. |
| 5,244,463 | A | 9/1993 | Cordner, Jr. et al. |
| 5,254,096 | A | 10/1993 | Rondelet et al. |
| 5,256,157 | A | 10/1993 | Samiotes et al. |
| 5,261,884 | A | 11/1993 | Stern et al. |
| 5,265,431 | A | 11/1993 | Gaudet et al. |
| 5,279,556 | A | 1/1994 | Goi et al. |
| 5,290,239 | A | 3/1994 | Classey et al. |
| 5,295,966 | A | 3/1994 | Stern et al. |
| 5,295,967 | A | 3/1994 | Rondelet et al. |
| 5,298,021 | A | 3/1994 | Sherer |
| 5,317,506 | A | 5/1994 | Coutré et al. |
| 5,330,431 | A | 7/1994 | Herskowitz |
| 5,336,245 | A | 8/1994 | Adams et al. |
| 5,338,157 | A | 8/1994 | Blomquist |
| 5,341,291 | A | 8/1994 | Roizen et al. |
| 5,348,539 | A | 9/1994 | Herskowitz |
| 5,366,904 | A | 11/1994 | Qureshi et al. |
| 5,370,612 | A | 12/1994 | Maeda et al. |
| 5,374,251 | A | 12/1994 | Smith |
| 5,374,965 | A | 12/1994 | Kanno |
| 5,376,070 | A | 12/1994 | Purvis et al. |
| 5,378,231 | A | 1/1995 | Johnson et al. |
| 5,387,088 | A | 2/1995 | Knapp et al. |
| 5,389,078 | A | 2/1995 | Zalesky et al. |
| 5,395,320 | A | 3/1995 | Padda et al. |
| 5,397,222 | A | 3/1995 | Moss et al. |
| 5,423,746 | A | 6/1995 | Burkett et al. |
| 5,429,602 | A | 7/1995 | Hauser |
| 5,431,627 | A | 7/1995 | Pastrone et al. |
| 5,437,635 | A | 8/1995 | Fields et al. |
| 5,462,051 | A | 10/1995 | Oka et al. |
| 5,482,446 | A | 1/1996 | Williamson et al. |
| 5,485,408 | A | 1/1996 | Blomquist |
| 5,501,665 | A | 3/1996 | Jhuboo et al. |
| 5,503,538 | A | 4/1996 | Wiernicki et al. |
| 5,507,412 | A | 4/1996 | Ebert et al. |
| 5,511,951 | A | 4/1996 | O'Leary |
| 5,513,957 | A | 5/1996 | O'Leary |
| 5,522,798 | A | 6/1996 | Johnson et al. |
| 5,522,799 | A | 6/1996 | Furukawa |
| 5,531,680 | A | 7/1996 | Dumas et al. |
| 5,531,697 | A | 7/1996 | Olsen et al. |
| 5,533,981 | A | 7/1996 | Mandro et al. |
| 5,545,140 | A | 8/1996 | Conero et al. |
| 5,547,470 | A | 8/1996 | Johnson et al. |
| 5,549,460 | A | 8/1996 | O'Leary |
| 5,551,850 | A | 9/1996 | Williamson et al. |
| 5,554,115 | A | 9/1996 | Thomas et al. |
| 5,562,621 | A | 10/1996 | Claude et al. |
| 5,566,098 | A * | 10/1996 | Lucente et al. ............. 361/681 |
| 5,573,502 | A | 11/1996 | LeCocq et al. |
| 5,573,506 | A | 11/1996 | Vasko |
| D376,848 | S | 12/1996 | Zeilig et al. |
| 5,588,815 | A | 12/1996 | Zaleski, II |
| 5,601,420 | A | 2/1997 | Warner et al. |
| 5,609,575 | A | 3/1997 | Larson et al. |
| 5,620,312 | A | 4/1997 | Hyman et al. |
| 5,628,619 | A | 5/1997 | Wilson |
| 5,630,710 | A | 5/1997 | Tune et al. |
| D380,260 | S | 6/1997 | Hyman |
| 5,637,093 | A | 6/1997 | Hyman et al. |
| 5,647,853 | A | 7/1997 | Feldmann et al. |
| 5,647,854 | A | 7/1997 | Olsen et al. |
| 5,669,877 | A | 9/1997 | Blomquist |
| 5,681,285 | A | 10/1997 | Ford et al. |
| 5,683,367 | A | 11/1997 | Jordan et al. |
| 5,685,844 | A | 11/1997 | Marttila |
| 5,695,473 | A | 12/1997 | Olsen |
| D390,654 | S | 2/1998 | Alsberg et al. |
| 5,713,856 | A | 2/1998 | Eggers et al. |
| 5,745,378 | A | 4/1998 | Barker et al. |
| 5,752,976 | A | 5/1998 | Duffin et al. |
| 5,766,155 | A | 6/1998 | Hyman et al. |
| 5,776,345 | A | 7/1998 | Truitt et al. |
| 5,782,805 | A | 7/1998 | Meinzer et al. |
| 5,788,669 | A | 8/1998 | Peterson |
| 5,788,851 | A * | 8/1998 | Kenley et al. ............. 210/739 |
| 5,791,880 | A | 8/1998 | Wilson |
| 5,795,327 | A | 8/1998 | Wilson et al. |

| | | |
|---|---|---|
| 5,807,322 A | 9/1998 | Lindsey et al. |
| 5,807,336 A | 9/1998 | Russo et al. |
| 5,813,972 A | 9/1998 | Nazarian et al. |
| 5,814,015 A | 9/1998 | Gargano et al. |
| 5,842,841 A | 12/1998 | Danby et al. |
| 5,871,465 A | 2/1999 | Vasko |
| 5,885,245 A | 3/1999 | Lynch et al. |
| 5,894,273 A | 4/1999 | Meador et al. |
| 5,895,371 A | 4/1999 | Levitas et al. |
| 5,897,530 A | 4/1999 | Jackson |
| 5,904,668 A | 5/1999 | Hyman et al. |
| 5,935,099 A | 8/1999 | Peterson et al. |
| 5,935,106 A | 8/1999 | Olsen |
| 5,943,633 A | 8/1999 | Wilson et al. |
| 5,951,510 A | 9/1999 | Barak |
| 5,993,420 A | 11/1999 | Hyman et al. |
| 6,004,020 A | 12/1999 | Bartur |
| 6,024,539 A | 2/2000 | Blomquist |
| 6,135,949 A | 10/2000 | Russo et al. |
| 6,145,695 A | 11/2000 | Garrigues |
| 6,173,198 B1 | 1/2001 | Schulze et al. |
| 6,203,528 B1 | 3/2001 | Deckert et al. |
| 6,231,560 B1 | 5/2001 | Bui et al. |
| 6,297,795 B1 | 10/2001 | Kato et al. |
| 6,348,952 B1 | 2/2002 | Jeong |
| 6,358,225 B1 | 3/2002 | Butterfield |
| 6,423,035 B1 | 7/2002 | Das et al. |
| 6,458,102 B1 | 10/2002 | Mann et al. |
| 6,475,180 B1 | 11/2002 | Peterson et al. |
| 6,485,465 B1 | 11/2002 | Moberg et al. |
| 6,500,151 B1 | 12/2002 | Cobb et al. |
| 6,585,675 B1 | 7/2003 | O'Mahony et al. |
| 6,592,551 B1 | 7/2003 | Cobb |
| 6,658,276 B1 * | 12/2003 | Pishney et al. ............. 600/322 |
| 2001/0031944 A1 | 10/2001 | Peterson et al. |
| 2001/0034502 A1 | 10/2001 | Moberg et al. |
| 2002/0004645 A1 | 1/2002 | Carlisle et al. |
| 2002/0044059 A1 * | 4/2002 | Reeder et al. ........... 340/573.1 |
| 2002/0120470 A1 * | 8/2002 | Trice, Sr. ....................... 705/3 |
| 2002/0128606 A1 | 9/2002 | Cowan et al. |
| 2002/0165491 A1 | 11/2002 | Reilly |
| 2003/0009133 A1 | 1/2003 | Ramey |
| 2003/0052787 A1 * | 3/2003 | Zerhusen et al. ........ 340/573.1 |
| 2003/0060754 A1 | 3/2003 | Reilly et al. |
| 2003/0060768 A1 | 3/2003 | Kiyatake et al. |
| 2003/0065287 A1 | 4/2003 | Spohn et al. |
| 2003/0073954 A1 | 4/2003 | Moberg et al. |
| 2003/0078534 A1 | 4/2003 | Hochman et al. |
| 2003/0097092 A1 | 5/2003 | Flaherty |
| 2003/0149402 A1 | 8/2003 | Gerlach et al. |

FOREIGN PATENT DOCUMENTS

| | | |
|---|---|---|
| EP | 0 215 249 A1 | 3/1987 |
| EP | 0 447 985 A1 | 9/1991 |
| EP | 0 522 527 A1 | 1/1993 |
| EP | 0 560 270 A2 | 9/1993 |
| EP | 0 567 944 A1 | 11/1993 |
| EP | 0 567 945 A1 | 11/1993 |
| EP | 0 567 946 A2 | 11/1993 |
| EP | 0 567 946 A3 | 11/1993 |
| EP | 0 567 962 A1 | 11/1993 |
| GB | 2190145 A | 11/1987 |
| GB | 2208897 A | 4/1989 |
| GB | 2 336 510 A | 10/1999 |
| WO | WO 84/04685 A1 | 12/1984 |
| WO | WO 92/03658 A1 | 3/1992 |
| WO | WO 93/05829 A1 | 4/1993 |
| WO | WO 95/17913 A1 | 7/1995 |
| WO | WO 00/42911 A1 | 7/2000 |
| WO | WO 00/48112 A2 | 8/2000 |
| WO | WO 00/68766 A1 | 11/2000 |

OTHER PUBLICATIONS

International Search Report for International Application No. PCT/US02/36964 of Applicant Baxter International Inc.

* cited by examiner

DUAL ORIENTATION DISPLAY FOR A MEDICAL DEVICE

DESCRIPTION

1. Technical Field

The present invention generally relates to a medical device such as an infusion pump, and in particular, to an infusion pump with a dual orientation display having both portrait and landscape modes of viewing.

2. Background of the Invention

It is typical for a medical device to have a display screen that displays data such as operating parameters. One type of medical device is an infusion pump. Infusion pumps as used in the field of health care are electromechanical devices that control the flow rate of medical fluids. The pumps can deliver drugs at a precise rate that maintains the drug concentration within a therapeutic margin and out of an unnecessary or possibly toxic range. Basically, the medical pumps provide appropriate drug delivery to the patient at a controllable rate that does not require frequent attention. Types of infusion pumps include syringe pumps, volumetric pumps, and ambulatory pumps.

A syringe pump operates a medical syringe to deliver a drug to a patient at a controlled rate. This pump employs an active fluid pumping mechanism, i.e., positive displacement of the syringe plunger, to expel fluid from the syringe.

A volumetric pump is used with an intravenous fluid administration set having a fluid source and an intravenous (IV) line connecting the fluid source to the patient. The pump is operatively associated with the intravenous line to influence the rate of fluid flow to the patient. For instance, the pump may have a plurality of actuators or fingers for massaging the intravenous line, thus controlling the flow rate of fluid through the line.

Ambulatory pumps typically include a pump control unit and drive mechanism including a variety of operating controllers adapted to accept a disposable pump chamber assembly. The pumping mechanism can include, for example, inlet and outlet valves and a liquid displacement plunger. Each pumping cycle in this type of pump begins with the outlet valve closed and the inlet valve open. Fluid flows from a source container into the section of tubing disposed between the inlet and outlet valve. After this section of tubing has filled with liquid, the inlet valve closes and the outlet valve opens. The plunger then compresses the short section of tubing between the valves, displacing the liquid contained therein and forcing it though the pump.

Medical devices and pumps are sometimes capable of being mounted to another medical device, machine, apparatus, bed, stretcher, wall, shelf, desk, etc. Many of these mountable medical devices and pumps are adaptable for mounting in various positions, e.g., vertically, horizontally, laterally, etc. Some of these mountable medical devices and pumps utilize a display for providing information. Often times the display is only readily viewable in one specific orientation. For instance, a vertically positioned medical device cooperating with a vertically orientated display, or a horizontally positioned medical device with a horizontally viewable display. Although various mounting options are available for the medical device, a display being readily viewable in only one orientation severely limits the flexibility of the device, e.g., a variably mountable medical device with a vertically oriented display. Use of a medical device or pump having a sole oriented display can require a viewer to expend unnecessary effort to position oneself for viewing the information displayed. Regardless of the type of mounting options available to a medical device having a display, it is desirable that the display be adaptable for easy viewing.

The present invention is provided to solve these and other problems.

SUMMARY OF THE INVENTION

Generally, the present invention is directed to a display for a medical device. The device is capable of being configured in various orientations. In one embodiment, the device comprises an infusion pump for dispensing a medical fluid to a patient. A controller is operably connected to the infusion pump. The controller controls the infusion pump. The display is operably connected to the controller and attached to the pump. The display is operably responsive to the orientation of the apparatus.

Another embodiment of the present invention is an infusion pump capable of being configured for mounting in various positions. The infusion pump comprises a controller being operably connected to the pump. A display is connected to the controller and attached to the infusion pump. The display is responsive to the orientation of the infusion pump.

According to another aspect of the present invention, an infusion pump is capable of being configured in several orientations. The pump has a display wherein the orientation of the display is rotated to accommodate viewing of the display in response to the orientation of the apparatus. The display provides graphics to facilitate a user's interaction with the apparatus, i.e., control, monitoring, operating, etc.

Other advantages and features of the present invention will be apparent from the following description of the specific embodiments illustrated in the accompanying drawings.

DETAILED DESCRIPTION

While this invention is susceptible of embodiments in many different forms, there is shown in the drawings and will herein be described in detail preferred embodiments of the invention. The present disclosure is to be considered as an exemplification of the principles of the invention and is not intended to limit the broad aspect of the invention to the embodiments illustrated.

As shown in FIGS. 1–5, in a preferred embodiment, the apparatus 10 of the present invention includes an infusion pump 12 for dispensing a fluid. Preferably, the apparatus 10 is utilized for dispensing a medical fluid to a person. While the pump 12 can take many different forms, in a most preferred embodiment, the pump 12 is generally in the form as described in commonly-owned U.S. patent application Ser. No. 10/172,807 entitled, "Infusion Pump," filed concurrently herewith and incorporated by reference herein, and commonly-owned U.S. patent application Ser. No. 10/172, 808 entitled, "System And Method For Operating An Infusion Pump," filed concurrently herewith and incorporated by reference herein. It is further understood that the apparatus 10 of the present invention can include other devices such as monitors including blood pressure monitors, EKG monitors and ECG monitors.

The apparatus 10 generally comprises a pump 12 having among other things, a controller 14 and a display 16. The controller 14 is operably connected to the pump 12. The controller 14 can be a micro-processor or a programmable logic controller. The controller 14 provides a means for controlling the pump 12. A display 16 is connected to the controller 14 and is preferably attached to the apparatus 10. The orientation of the display 16 is capable of being positioned in response to the various mounting configurations of the pump 12.

Figure 1:
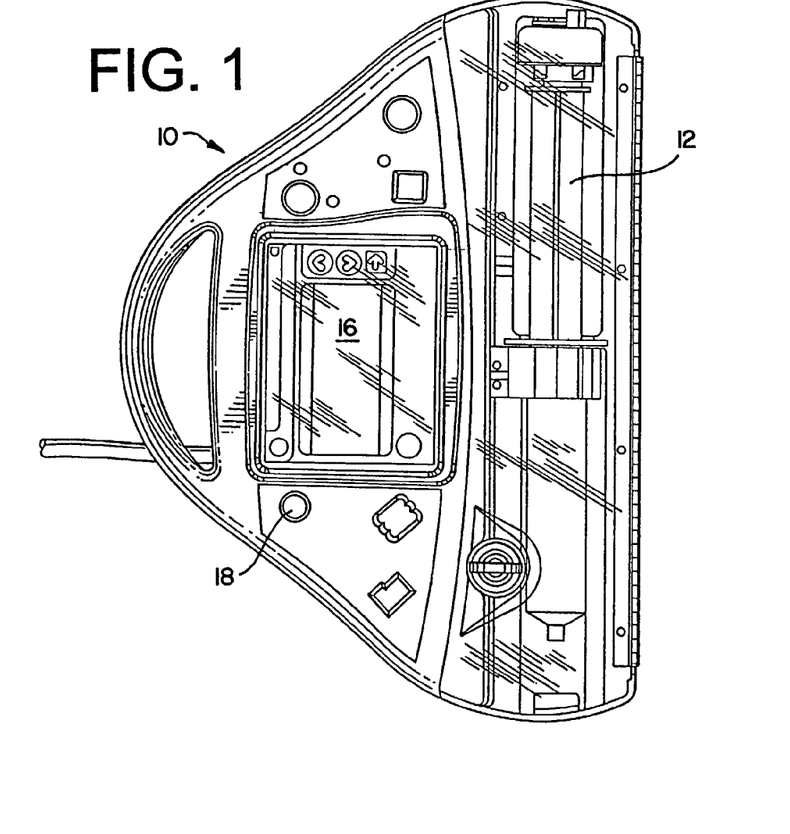
FIG. 1 depicts an embodiment of the present invention.
Figure 2A:
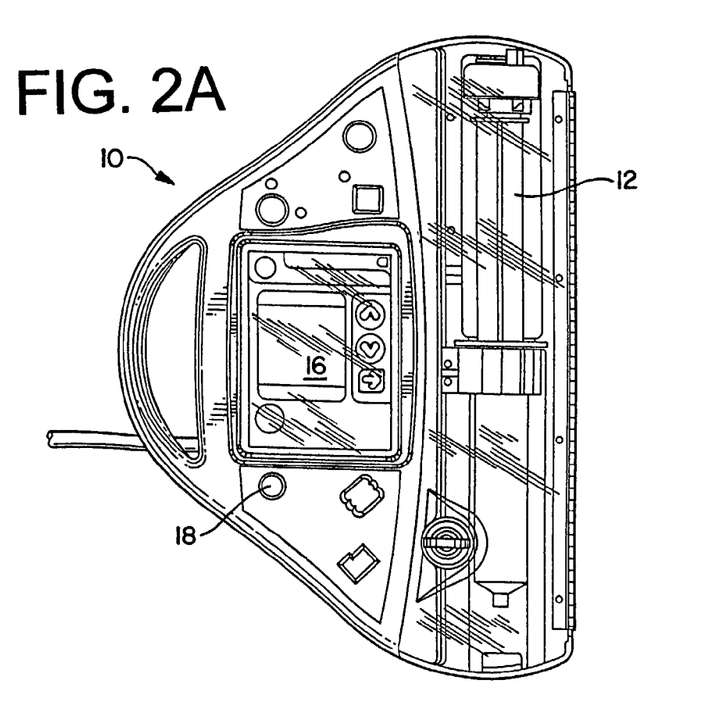
FIG. 2a illustrates an apparatus of the present invention in a generally vertical mounting configuration.
Figure 2B:
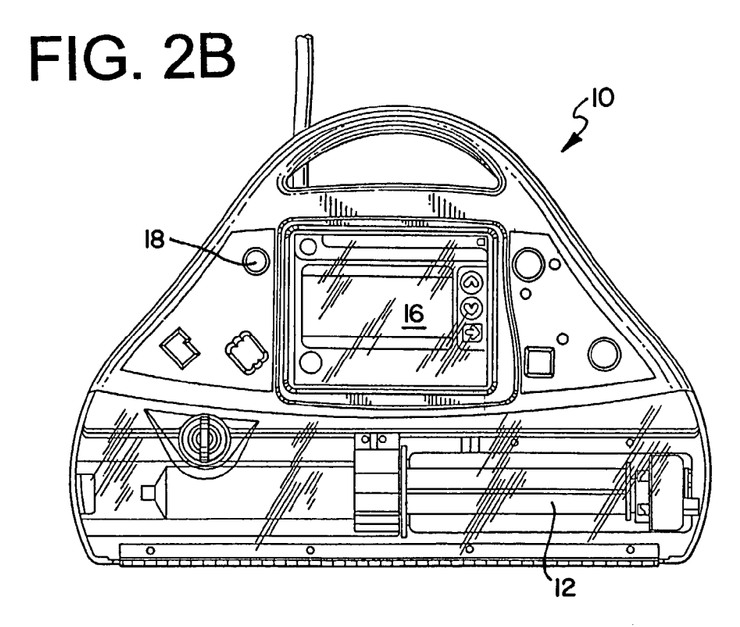
FIG. 2b illustrates an apparatus of the present invention in a generally horizontal mounting configuration.
Figure 3:
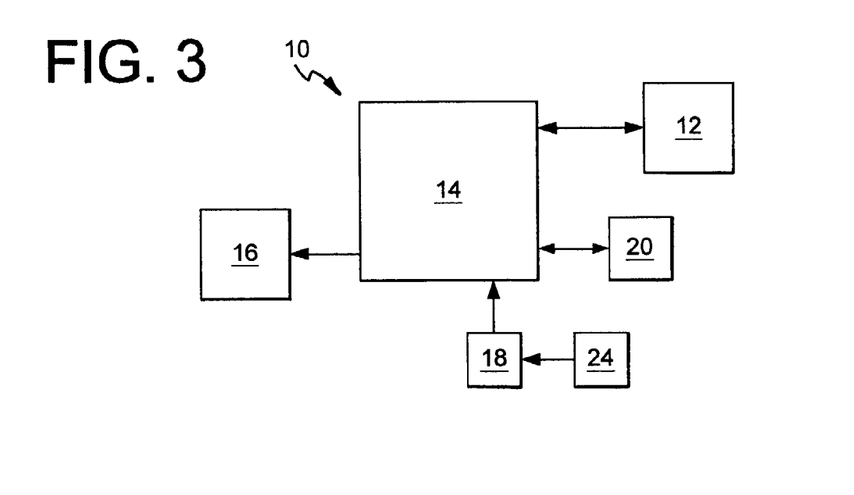
FIG. 3 is a block diagram depicting one embodiment of the present invention.

The pump 12 is capable of being mounted in several configurations. Generally, the pump 12 is mounted in either a vertical position (FIG. 2a) or a horizontal position (FIG. 2b). The display screen 16 displays any of the monitoring, controlling, and operating information related to the pump 12. A switch 18 can be manually actuated to change the orientation of the graphical information displayed on the screen 16. Actuation of the switch 18 can rotate the information displayed on the screen 16 in 1° increments between 0° and 360°. Preferably, a single actuation of the switch 18 will rotate the orientation of the display 90°.

Figure 4:
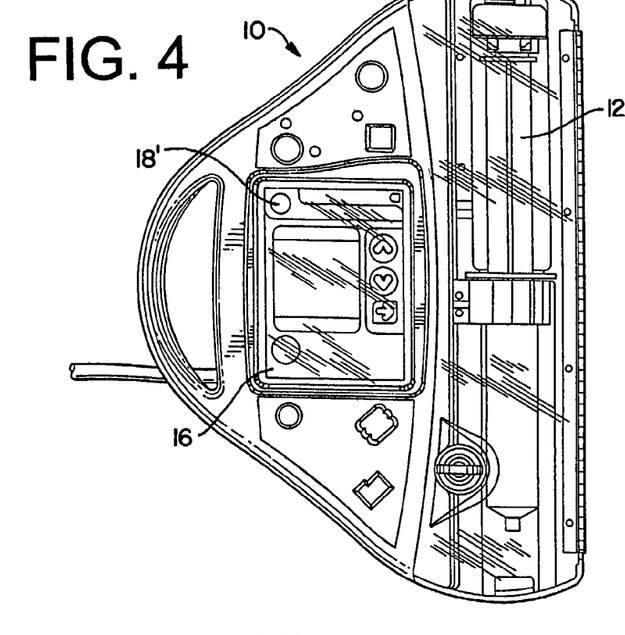
FIG. 4 illustrates another embodiment of the present invention.
Figure 5:
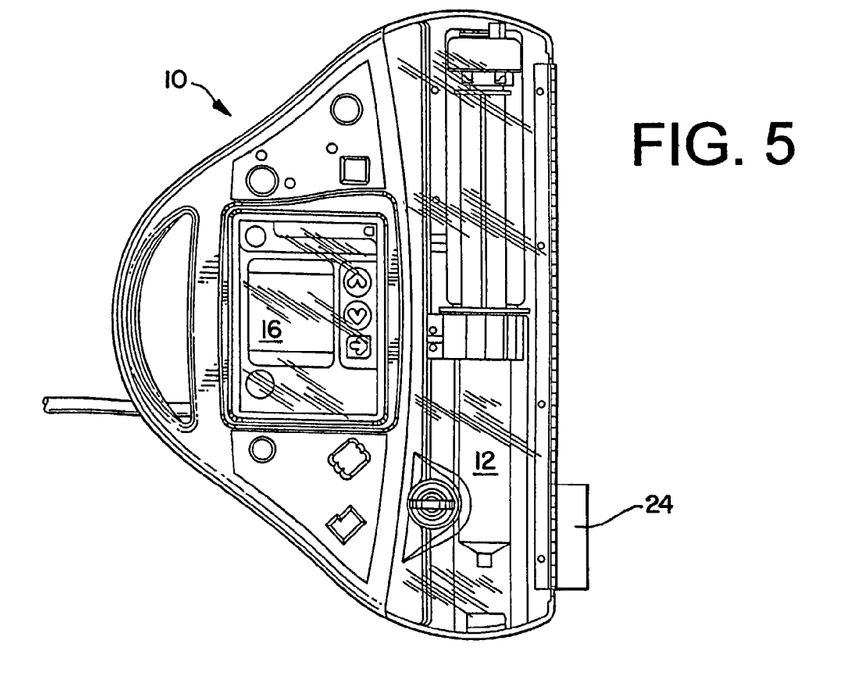
FIG. 5 illustrates another embodiment of the present invention.

As shown in FIG. 4, the display screen 16 can also include a touch-sensitive transparent panel or data entry device, e.g., graphical button 18', covering a monochrome or color liquid crystal display 16 for actuation by the operator. The soft-key switch 18' defined on the display 16 provides a natural interface for selecting objects or buttons presented on the display. The switch 18' is responsive to the touch of a finger or a stylus (not shown) on the screen panel over the object or button to be selected. Similar to the manual switch 18, actuation of the touch screen switch 18' will rotate the graphic displayed on the screen 16, preferably in 90° increments. Although the manual switch 18 is shown as being integrated within the apparatus 10 or the display 16, it is to be understood that the switch is operably connected to the display and can be remote from the apparatus, e.g., remote wired connection or wireless interaction.

As mentioned earlier, the pump 12 is preferably mounted in either a generally vertical position (FIG. 2a) or a generally horizontal position (FIG. 2b). A software program executes the operations of the pump 12 and includes a section directed to the display screen 16, e.g., user interface. The display screen 16 provides for the display of information on the screen. Preferably, the information is displayed in either a landscape orientation or a portrait orientation. When the apparatus 10 is mounted in the vertical configuration as shown in FIG. 2a, information is displayed on the display screen 16 in a portrait configuration. Alternatively, when the apparatus 10 is mounted in the horizontal configuration as shown in FIG. 2b, information is displayed on the display screen 16 in a landscape configuration. Thus, in response to the mounting configuration of the apparatus 10, the information displayed on the screen 16 can be positioned in an orientation in cooperation with the apparatus so that the displayed information can be viewed by a user without the need to adjust one's viewing position, i.e., tilting one's head.

The apparatus 10 may also include a memory 20. As discussed, the apparatus 10 includes a controller 14, e.g., a central processing unit. The controller 14 is operably connected to the memory 20. Loaded onto the memory 20 of the apparatus 10 is an application or program. When the application is executed by the central processing unit 14, the pump 12 performs at the direction of the user. These tasks can include displaying a graphic related the control, monitor, and operation of the pump 12 on the touch screen 16.

Upon initial execution of the application by the controller 14, the apparatus 10 provides a switch 18 on the touch screen 16 for allowing the user the ability to rotate the information displayed on the screen 16, preferably in 90° increments.

An alternative embodiment of the present invention includes a sensor 24 being operably connected to the switch 18. It is to be understood that the switch 18 can be a hardware switch or a software switch wherein the execution of an event, i.e., the actuation of the sensor 24, triggers the switch 18. One embodiment of the present invention is directed to a sensor 24 being responsive to gravitation wherein movement of the pump 12, i.e., from a generally vertical position to a generally horizontal position, and vice-versa, affects the sensor 24 and thus, affects the switch wherein the display 16 is automatically adjusted accordingly.

The orientation of the display shown on the screen 16 is selectable by a user. Preferably, the user can select and/or edit the information displayed on the screen 16, i.e., actuating soft-key buttons on the apparatus 10 or the touch screen. The user can selectively view a variety of information stored within the apparatus 10 by actuating the button associated with the topic. Furthermore, the user is capable of selecting the type of information displayed by editing the program executed by the apparatus.

While the specific embodiments have been illustrated and described, numerous modifications come to mind without significantly departing from the spirit of the invention and the scope of protection is only limited by the scope of the accompanying claims.

What is claimed is:

1. An infusion pump comprising:
 a housing;
 a controller being operably connected to the housing, the controller for controlling the device;
 an output to a patient extending from a surface of the housing; and
 a display being operably connected to the controller and supported by the housing, the display being operably responsive to the orientation of the device, so that information displayed by the display can be oriented right-side-up regardless of whether the surface from which the output extends is mounted in a first orientation or a second orientation.

2. The infusion pump of claim 1 wherein the controller is a programmable logic controller.

3. The infusion pump of claim 1 wherein the controller is a micro-processor.

4. The infusion pump of claim 1 wherein the display includes switch, the display operably responsive to the switch.

5. The infusion pump of claim 4 wherein the switch is integral with the screen, the switch being responsive to contact by a human finger.

6. The infusion pump of claim 4 wherein the switch is integral with the screen, the switch being responsive to contact by a stylus.

7. The infusion pump of claim 1 wherein the display is capable of orientation in one of a landscape orientation and a portrait orientation.

8. The infusion pump of claim 1 wherein the display rotates 90°.

9. The infusion pump of claim 1 wherein the display rotates 180°.

10. The infusion pump of claim 1 wherein the display rotates 270°.

11. An apparatus for dispensing a medical fluid to a person, the apparatus being adaptable for configuration in various orientations, the apparatus comprising:
   an infusion pump for dispensing the medical fluid in an initial direction to the person;
   a controller being operably connected to the infusion pump, the controller for controlling the infusion pump; and,
   a display being operably connected to the controller and attached to the pump, the display being operably responsive to the orientation of the apparatus, so that information displayed by the display can be oriented right-side-up regardless of whether the initial direction of the medical fluid from the pump is dispensed in a first direction or a second direction.

12. The apparatus of claim 11 wherein the controller is a programmable logic controller.

13. The apparatus of claim 11 wherein the controller is a micro-processor.

14. The apparatus of claim 11 wherein the display includes a switch, the display operably responsive to the switch.

15. The apparatus of claim 14 wherein the switch is integral with the screen, the switch being responsive to contact by a human finger.

16. The apparatus of claim 14 wherein the switch is integral with the screen, the switch being responsive to contact by a stylus.

17. The apparatus of claim 11 wherein the display is capable of orientation in one of a landscape orientation and a portrait orientation.

18. An apparatus for dispensing a medical fluid to a person and being configurable for mounting in various positions, the apparatus comprising:
   an infusion pump for dispensing the medical fluid to the person;
   a controller being operably connected to the pump for controlling the pump; and
   a display being operably connected to the controller, the display being adaptable by an operator of the pump for repositioning in response to the various mounting positions of the pump so that the operator can be hands-free from the apparatus and view information on the display right-side-up without tilting his/her head.

19. The apparatus of claim 18 wherein the display includes a screen responsive to contact thereon.

20. The apparatus of claim 19 wherein the display is responsive to contact by a human finger.

21. The apparatus of claim 19 wherein the display is responsive to contact by a stylus.

22. The apparatus of claim 18 wherein the display includes a plurality of display positions.

23. The apparatus of claim 18 wherein the display comprises an image.

24. The apparatus of claim 18 wherein the pump is portable.

25. The apparatus of claim 18 further including a switch being operably connected to the display, the display being responsive to the switch wherein orientation of the display being adaptable for alteration in response to activation of the switch.

26. The apparatus of claim 25 wherein the switch is integrated within the display screen.

27. The apparatus of claim 25 wherein the switch is responsive to gravity.

28. An infusion pump for dispensing a medical fluid to a person, the person being operably connected to the pump, the infusion pump comprising:
   a controller contained within the infusion pump;
   a display operably connected to the controller and attached to the pump; and
   a switch, the display operably responsive to the switch to rotate the display, so that an operator of the pump can select the switch causing the display to show information right-side-up regardless of whether the pump is oriented in a first position or second position.

29. The infusion pump of claim 28 wherein the display includes a screen responsive to contact thereon.

30. The infusion pump of claim 29 wherein the switch is integral with the screen, the switch being responsive to contact by a human finger.

31. The infusion pump of claim 29 wherein the switch is integral with the screen, the switch being responsive to contact by a stylus.

32. The infusion pump of claim 28 wherein the display rotates 90°.

33. The infusion pump of claim 28 wherein the display rotates 180°.

34. The infusion pump of claim 28 wherein the display rotates 270°.

35. The infusion pump of claim 28 wherein the range of rotation of the display screen is approximately between 0° and 360°.

36. The infusion pump of claim 28 wherein the switch further comprises:
   a sensor, the sensor being operably responsive to the orientation of the apparatus wherein the controller rotates the display in response to the sensor and the switch.

37. The infusion pump of claim 36 wherein the sensor is responsive to gravity.

38. The infusion pump of claim 28 wherein the controller is a programmable logic controller.

39. The infusion pump of claim 28 wherein the controller is a micro-processor.

* * * * *

(12) EX PARTE REEXAMINATION CERTIFICATE (8573rd)

United States Patent
Gillespie, Jr. et al.

(10) Number: US 6,997,905 C1
(45) Certificate Issued: Sep. 27, 2011

(54) DUAL ORIENTATION DISPLAY FOR A MEDICAL DEVICE

(75) Inventors: John Gillespie, Jr., Libertyville, IL (US); Thomas A. McGraghan, Libertyville, IL (US)

(73) Assignee: Baxter International Inc., Deerfield, IL (US)

Reexamination Request:
No. 90/009,778, Jul. 8, 2010

Reexamination Certificate for:
Patent No.: 6,997,905
Issued: Feb. 14, 2006
Appl. No.: 10/172,804
Filed: Jun. 14, 2002

(51) Int. Cl.
*A61M 1/00* (2006.01)

(52) U.S. Cl. ........................................................ 604/151
(58) Field of Classification Search .................. None
See application file for complete search history.

(56) References Cited

U.S. PATENT DOCUMENTS

| 4,676,776 | A | 6/1987 | Howson |
| 5,868,710 | A | 2/1999 | Battiato et al. |
| 6,154,214 | A | 11/2000 | Uyehara et al. |
| 6,584,336 | B1 * | 6/2003 | Ali et al. ...................... 600/323 |
| 2001/0044602 | A1 | 11/2001 | Angersbach et al. |

* cited by examiner

*Primary Examiner* — Jeanne M Clark (57) ABSTRACT

A medical device (10) is disclosed. The device (10) is adaptable for configuration in various positions. In the preferred embodiment, the device (10) comprises an infusion pump (12) for dispensing a medical fluid to a patient. A controller (14) is operably connected to a display (16) and the pump (12). The display (16) is operably responsive to the position of the pump (10) wherein information on the display (16) can be easily viewed.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-39 are cancelled.

* * * * *